US011576583B2

(12) United States Patent
Dana et al.

(10) Patent No.: US 11,576,583 B2
(45) Date of Patent: Feb. 14, 2023

(54) NONINVASIVE BLOOD PRESSURE MEASUREMENT METHOD AND DEVICE

(71) Applicant: Samsung Electronics Co., Ltd., Suwon-si (KR)

(72) Inventors: Alexandra Dana, Tel Aviv (IL); Jungmok Bae, Menlo Park, CA (US); Matthew Wiggins, San Jose, CA (US)

(73) Assignee: Samsung Electronics Co., Ltd.

( * ) Notice: Subject to any disclaimer, the term of this patent is extended or adjusted under 35 U.S.C. 154(b) by 871 days.

(21) Appl. No.: 16/010,289

(22) Filed: Jun. 15, 2018

(65) Prior Publication Data

US 2019/0298188 A1   Oct. 3, 2019

Related U.S. Application Data

(60) Provisional application No. 62/648,824, filed on Mar. 27, 2018.

(51) Int. Cl.
*A61B 5/021* (2006.01)
*A61B 5/00* (2006.01)
(Continued)

(52) U.S. Cl.
CPC ........ *A61B 5/02108* (2013.01); *A61B 5/0225* (2013.01); *A61B 5/02116* (2013.01);
(Continued)

(58) Field of Classification Search
CPC .............. A61B 5/02108; A61B 5/7221; A61B 5/02241; A61B 5/7253; A61B 5/1102;
(Continued)

(56) References Cited

U.S. PATENT DOCUMENTS 4,295,471 A * 10/1981 Kaspari .................. A61B 7/045
600/488
5,720,292 A * 2/1998 Poliac ..................... A61B 5/022
600/509
(Continued)

FOREIGN PATENT DOCUMENTS

EP         0181067 B1     7/1991
JP       2001178691 A     7/2001

OTHER PUBLICATIONS

M.A. Lyew et al., "Blood Pressure Measurement Using Oscillometric Finger Cuffs in Children and Young Adults", Anaesthesia, 1994, vol. 49, pp. 895-899, The Association of Anaesthetists of Great Britian and Ireland.
(Continued)

*Primary Examiner* — Jacqueline Cheng
*Assistant Examiner* — Tho Q Tran
(74) *Attorney, Agent, or Firm* — Innovation Counsel LLP

(57) ABSTRACT

A method for estimating blood pressure using a blood flow occlusion system applied to an artery includes receiving from a first sensor a sensed signal; processing at a processor the sensed signal to detect beats in a pulsatile signal; determining validity of the detected beats; storing the detected beats and data associated with the detected beats in the sensed signal as the pressure applied to the artery by the blood flow occlusion system deflates towards a level below a nominal level; determining baseline beat characteristics; evaluating the stored beats and associated data to detect change in beat characteristics as compared to the baseline beat characteristics; selecting a beat before the detected change in the beat characteristic as the last beat indicating the onset of the diastolic blood pressure for the artery; determining a value of the applied pressure at the last beat as the diastolic blood pressure for the artery.

24 Claims, 11 Drawing Sheets

(51) Int. Cl.
  A61B 5/022    (2006.01)
  A61B 5/11     (2006.01)
  A61B 8/04     (2006.01)
  A61B 8/08     (2006.01)
  A61B 5/0225   (2006.01)
  A61B 8/02     (2006.01)
  A61B 5/024    (2006.01)
  A61B 5/0245   (2006.01)

(52) U.S. Cl.
  CPC ...... *A61B 5/02125* (2013.01); *A61B 5/02241* (2013.01); *A61B 5/1102* (2013.01); *A61B 5/7221* (2013.01); *A61B 5/7253* (2013.01); *A61B 5/7278* (2013.01); *A61B 8/02* (2013.01); *A61B 8/04* (2013.01); *A61B 8/5223* (2013.01); *A61B 5/0245* (2013.01); *A61B 5/02416* (2013.01); *A61B 2562/0247* (2013.01)

(58) Field of Classification Search
  CPC ... A61B 8/04; A61B 5/02116; A61B 5/02125; A61B 8/02; A61B 5/7278; A61B 8/5223; A61B 5/0225; A61B 2562/0247; A61B 5/02416; A61B 5/0245; A61B 5/6826; A61B 5/02255; A61B 8/022; A61B 5/022; A61B 5/021; A61B 5/02225
  See application file for complete search history.

(56) References Cited

U.S. PATENT DOCUMENTS

| | | | |
|---|---|---|---|
| 6,647,287 B1* | 11/2003 | Peel, III | A61B 5/02125 600/485 |
| 7,544,168 B2 | 6/2009 | Nitzan | |
| 9,795,308 B2 | 10/2017 | Murray | |
| 2006/0052713 A1* | 3/2006 | Poliac | A61B 5/0235 600/490 |
| 2009/0299421 A1* | 12/2009 | Sawchuk | A61N 1/37 607/28 |
| 2011/0105918 A1* | 5/2011 | Fortin | A61B 5/0059 600/493 |
| 2011/0130667 A1* | 6/2011 | Inoue | A61B 5/02225 600/490 |
| 2012/0123280 A1* | 5/2012 | Romanovski | A61B 5/0225 600/485 |
| 2012/0245471 A1 | 9/2012 | Langewouters et al. | |
| 2013/0138001 A1 | 5/2013 | Wu | |
| 2013/0303923 A1* | 11/2013 | Lerner | A61B 5/02208 600/490 |
| 2014/0094666 A1 | 4/2014 | Fine | |
| 2015/0105637 A1* | 4/2015 | Yu | A61B 5/14552 600/324 |
| 2017/0119274 A1* | 5/2017 | Chakravarthy | A61B 5/366 |
| 2019/0104953 A1* | 4/2019 | Narasimhan | A61B 5/7235 |

OTHER PUBLICATIONS

Willem Jan W. Bos et al., "Reconstruction of Brachial Artery Pressure From Noninvasive Finger Pressure Measurements", Circulation, Oct. 15, 1996, vol. 94, No. 8, pp. 1870-1875, American Heart Association, Inc.

SH Song et al., "Estimation of Blood Pressure Using Photoplethysmography on the Wrist", Computers in Cardiology, 2009, vol. 36, pp. 741-744.

* cited by examiner

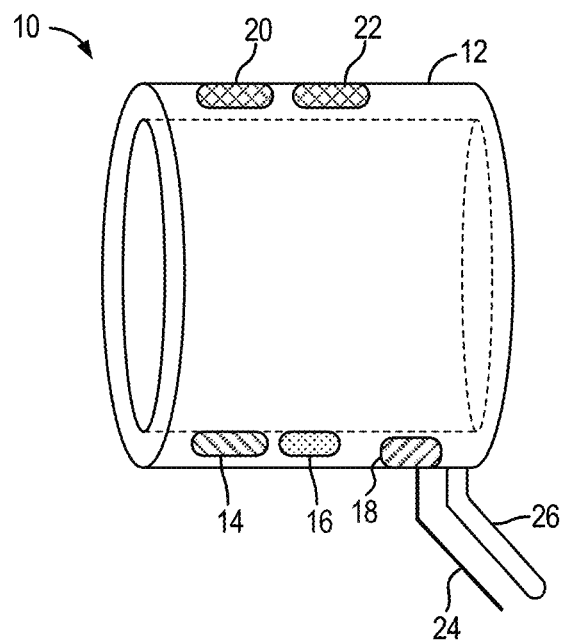
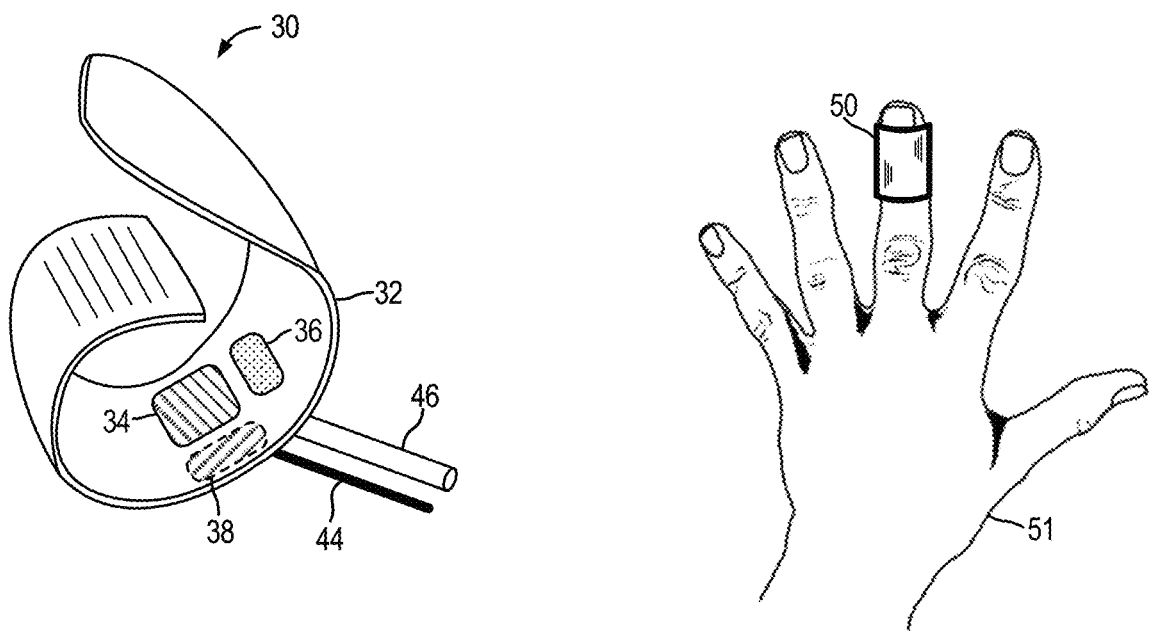
Fig. 1(a)
Fig. 1(b)　　　Fig. 1(c)
Fig. 1

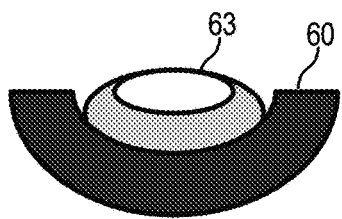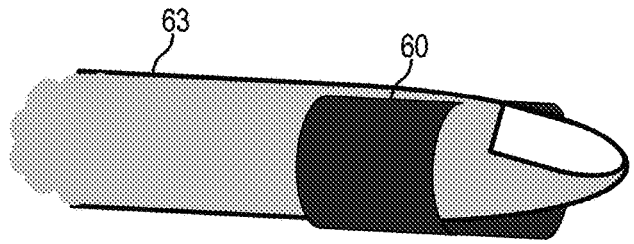
Fig. 2(a)    Fig. 2(b)
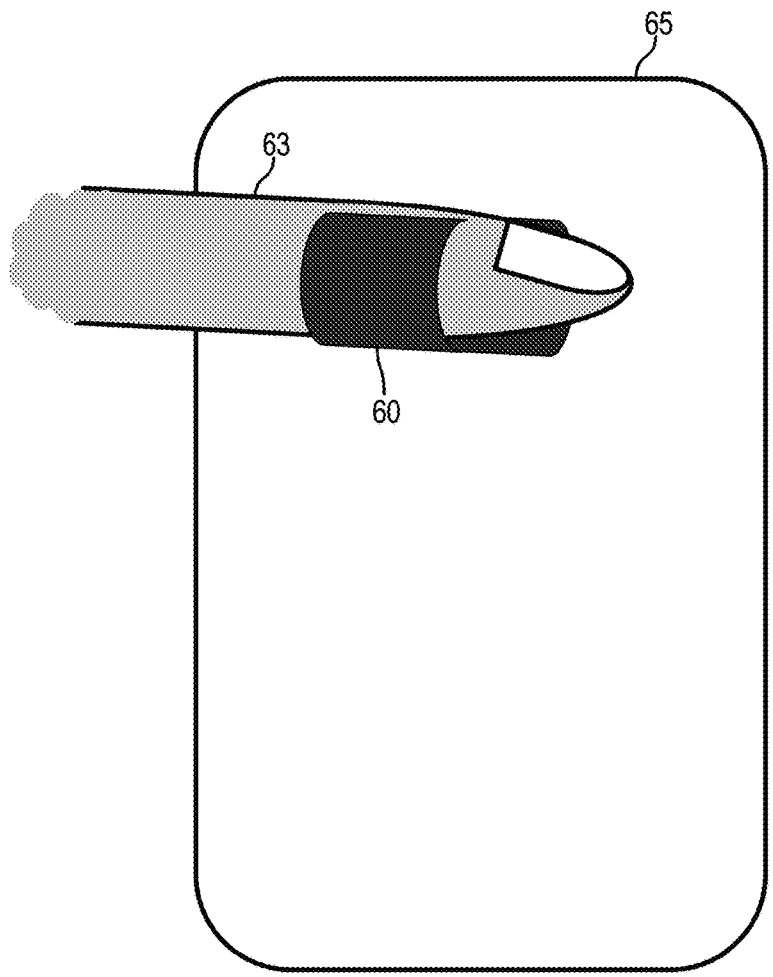
Fig. 2(c)
Fig. 2

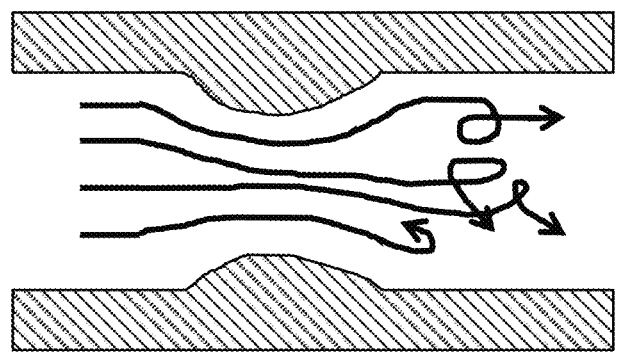
Fig. 6(a)
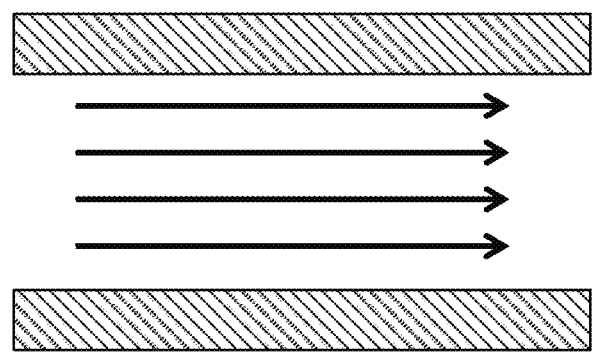
Fig. 6(b)
Fig. 6

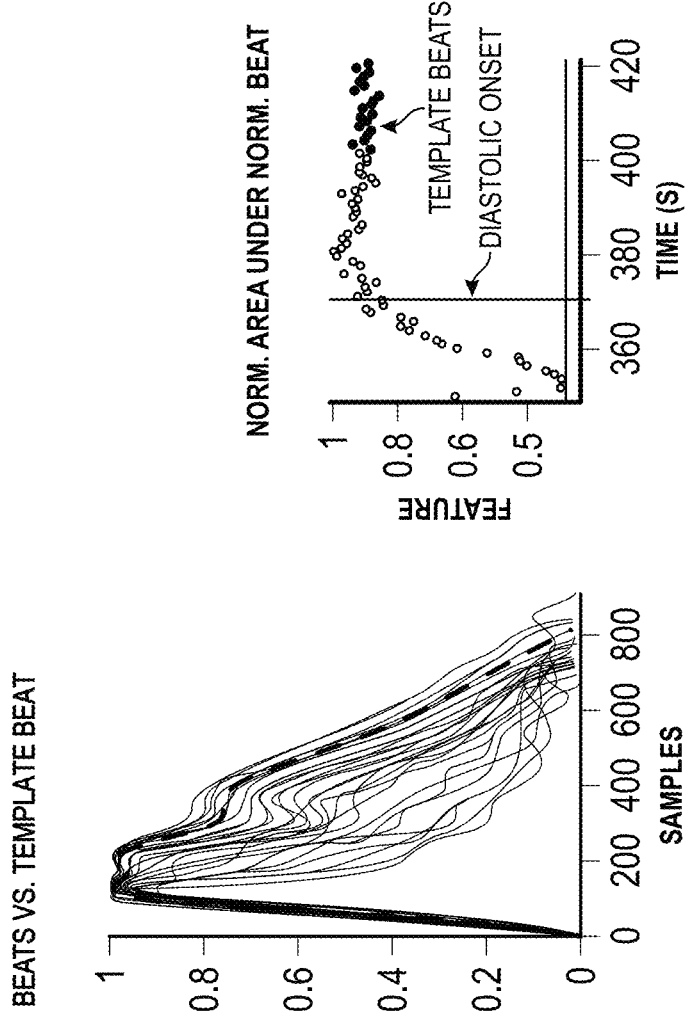
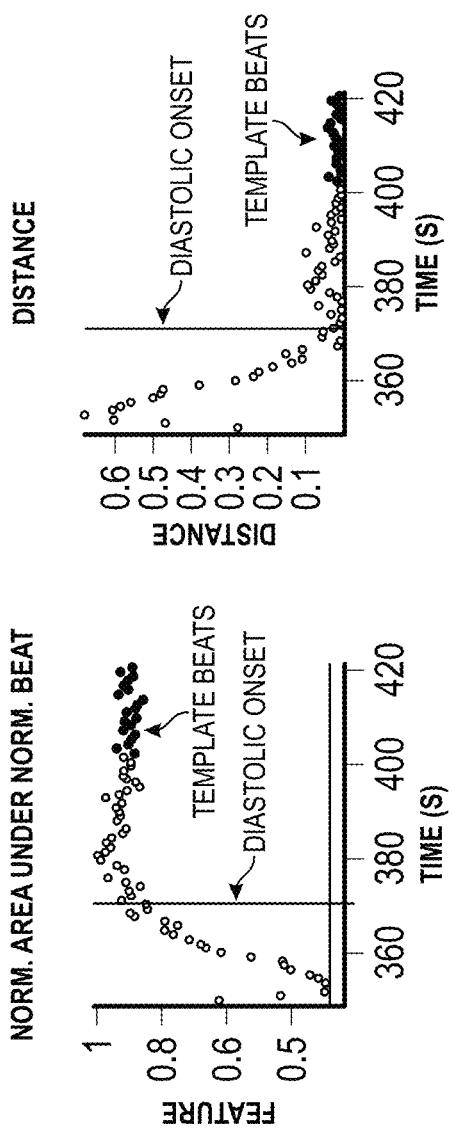
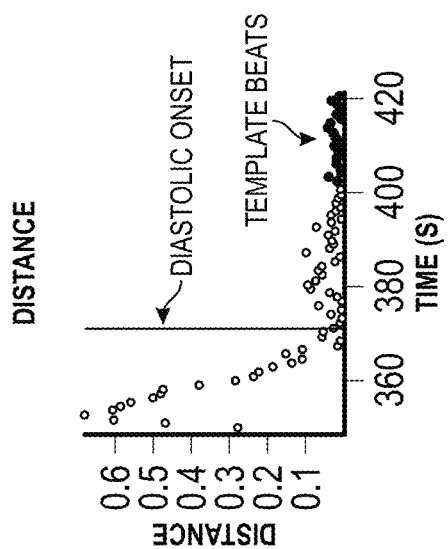
FIG. 11(a)
FIG. 11(b)
FIG. 11(c)
FIG. 11

NONINVASIVE BLOOD PRESSURE MEASUREMENT METHOD AND DEVICE

CROSS REFERENCE TO RELATED APPLICATIONS

This application claims priority to U.S. Provisional Patent Application No. 62/648,824, entitled NONINVASIVE BLOOD PRESSURE MEASUREMENT METHOD AND DEVICE, filed Mar. 27, 2018, which is incorporated herein by reference for all purposes.

FIELD

The present disclosure relates to a medical monitoring device and method thereof, and, in particular, to a system and method for noninvasive blood pressure measurement.

BACKGROUND

Prolonged hypertension is a major risk factor for heart disease, heart failure, heart attacks, stroke, kidney failure and shortened life expectancy. Frequently, individuals don't know that they have a problem due to infrequent or inaccurate blood pressure (BP) measurements. Traditional blood pressure measurement devices rely on brachial measurements using an arm cuff. The auscultatory method and the oscillometric method of measuring blood pressure using brachial arm cuffs are the most commonly used methods. Arm cuffs are bulky and can be uncomfortable to the users and the number of daily measurements that usually limited using these traditional methods.

Wearable device users can obtain feedback on the status of their own cardiovascular and mental health to enable them to make better near-term decisions to maximize their quality of life.

SUMMARY

The present disclosure discloses a device and method for blood pressure measurement substantially as shown in and/or described below, for example in connection with at least one of the figures, as set forth more completely in the claims.

These and other advantages, aspects and novel features of the present disclosure, as well as details of an illustrated embodiment thereof, will be more fully understood from the following description and drawings.

In one embodiment, a method for estimating blood pressure of a user by using a blood flow occlusion system applied to an artery in the body of the user, the method includes in response to a pressure being applied to the artery by the blood flow occlusion system to occlude blood flow in the artery and the pressure being released at a given rate, receiving from a first sensor a sensed signal; processing, at a processor, the sensed signal to detect beats in a pulsatile signal; in response to detecting beats in the pulsatile signal, determining validity of the detected beats; in response to detecting valid beats in the sensed signal, storing the detected beats and data associated with the detected beats in the sensed signal as the pressure applied to the artery by the blood flow occlusion system deflates towards a level below a nominal level; determining a baseline beat characteristic; evaluating the stored beats and associated data to detect change in beat characteristics as compared to the baseline beat characteristic; selecting a beat before the detected change in the beat characteristic as the last beat indicating the onset of the diastolic blood pressure for the artery; determining a value of the applied pressure at the last beat as the diastolic blood pressure for the artery; and providing the diastolic blood pressure as an output.

In another embodiment, a blood pressure measuring device for estimating blood pressure of a user by using a blood flow occlusion system applied to an artery in the body of the user includes a pressure application element configured to apply pressure to an artery to occlude blood flow in the artery and to release the pressure; a first sensor configured to sense pulsatile signal; and a processor configured to: in response to the pressure being applied to the artery by the pressure application element to occlude blood flow in the artery and the pressure being released at a given rate, receive from the first sensor a sensed signal; process the sensed signal to detect beats in a pulsatile signal; in response to detecting beats in the pulsatile signal, determine validity of the detected beats; in response to detecting valid beats in the sensed signal, store the detected beats and data associated with the detected beats in the sensed signal as the pressure applied to the artery by the blood flow occlusion system deflates towards a level below a nominal level; determine a baseline beat characteristic; evaluate the stored beats and associated data to detect change in beat characteristics as compared to the baseline beat characteristic; select a beat before the detected change in the beat characteristic as the last beat indicating the onset of the diastolic blood pressure for the artery; determine a value of the applied pressure at the last beat as the diastolic blood pressure for the artery; and provide the diastolic blood pressure as an output.

In another embodiment, a method for estimating blood pressure of a user by using a blood flow occlusion system applied to a finger of the user includes in response to a pressure being applied to an artery in the finger by the blood flow occlusion system to occlude blood flow in the artery and the pressure being released at a given rate, receiving from a first sensor implemented in the blood flow occlusion system a sensed signal from the finger; processing, at a processor, the sensed signal to detect beats in a pulsatile signal; in response to detecting beats in the pulsatile signal, determining validity of the detected beats; in response to detecting valid beats in the sensed signal, storing the detected beats and data associated with the detected beats in the sensed signal as the pressure applied to the artery by the blood flow occlusion system deflates towards a level below a nominal level; determining a baseline beat characteristic; evaluating the stored beats and associated data to detect change in beat characteristics as compared to the baseline beat characteristic; selecting a beat before the detected change in the beat characteristic as the last beat indicating the onset of the diastolic blood pressure for the artery; determining a value of the applied pressure at the last beat as the finger diastolic blood pressure; and providing the finger diastolic blood pressure as an output.

BRIEF DESCRIPTION OF THE DRAWINGS

Various embodiments of present disclosure are disclosed in the following detailed description and the accompanying drawings.

FIG. 1, which includes FIGS. 1(a) to 1(c), illustrates blood pressure measuring devices which can be used to implement the blood pressure measurement method in embodiments of the present disclosure.

FIG. 2, which includes FIGS. 2(a) to 2(c), illustrates another example of the blood pressure measuring device using a compression finger cuff.

FIG. 6, which includes FIGS. 6(a) and 6(b), illustrates the turbulent and laminar blood flow characteristics in some examples.

FIG. 11, which includes FIGS. 11(a) to 11(c), illustrates the return to shape operation in some examples.

DETAILED DESCRIPTION

Figure 3:
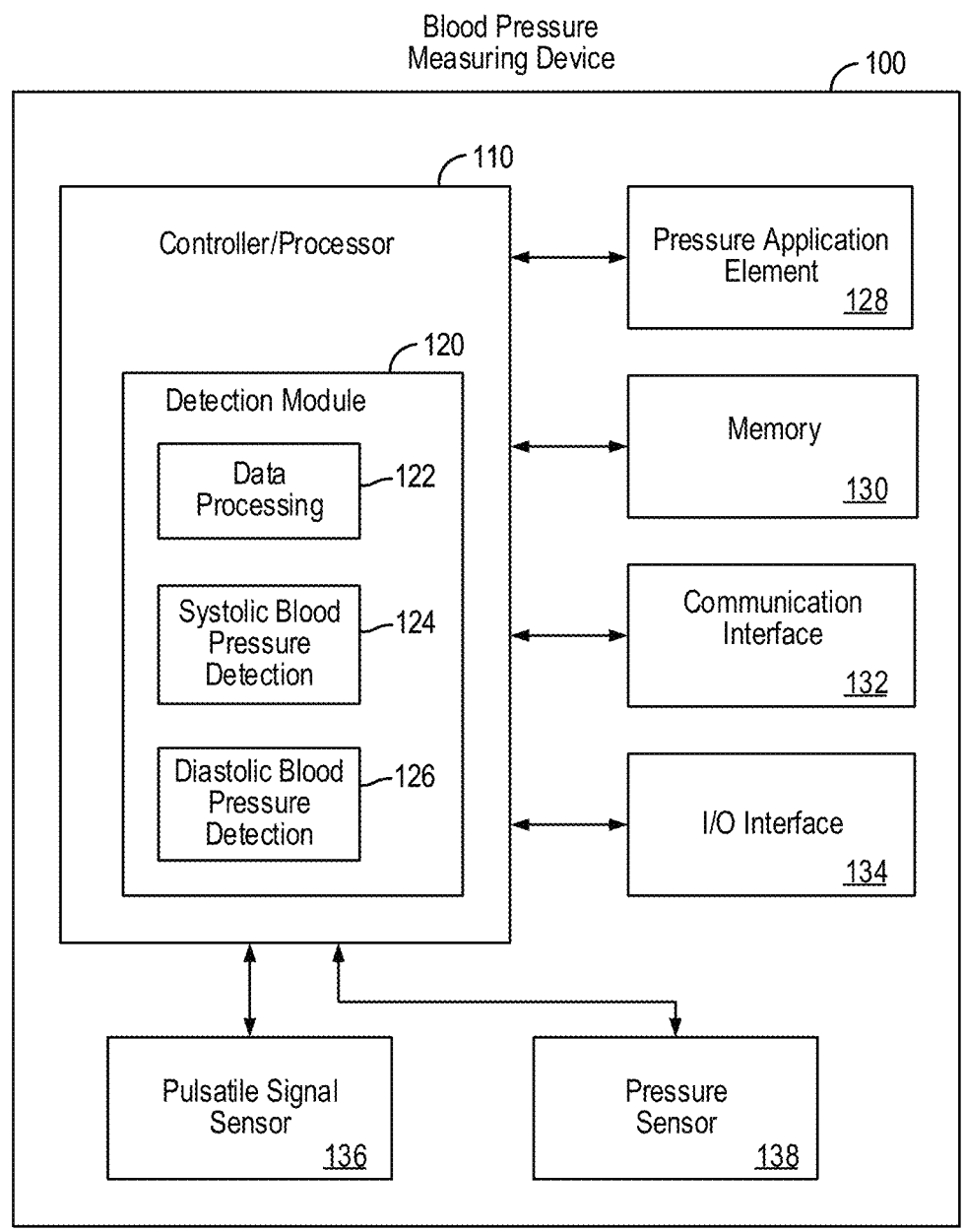
FIG. 3 illustrates a block diagram of a blood pressure measuring device in embodiments of the present disclosure.

Present disclosure can be implemented in numerous ways, including as a process; an apparatus; a system; a composition of matter; a computer program product embodied on a computer readable storage medium; and/or a processor, such as a hardware processor or a processor device configured to execute instructions stored on and/or provided by a memory coupled to the processor. In this specification, these implementations, or any other form that present disclosure may take, may be referred to as techniques. In general, the order of the steps of disclosed processes may be altered within the scope of present disclosure. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of present disclosure is provided below along with accompanying figures that illustrate the principles of present disclosure. Present disclosure is described in connection with such embodiments, but present disclosure is not limited to any embodiment. The scope of present disclosure is limited only by the claims and present disclosure encompasses numerous alternatives, modifications and equivalents. Numerous specific details are set forth in the following description in order to provide a thorough understanding of present disclosure. These details are provided for the purpose of example and present disclosure may be practiced according to the claims without some or all of these specific details. For the purpose of clarity, technical material that is known in the technical fields related to present disclosure has not been described in detail so that present disclosure is not unnecessarily obscured.

In embodiments of the present disclosure, a method for blood pressure measurement of a user determines the diastolic blood pressure using a return to shape analysis. In particular, after artery occlusion, the method detects and stores beats and data associated with the beats from a sensed pulsatile signal obtained as the applied pressure decreases. The method determines the onset of the diastolic blood pressure by comparing the beat characteristics of the stored beats to baseline beat characteristics and determining the applied pressure at which one or more selected beat characteristics change. The applied pressure at the point the beat characteristics change is taken as the diastolic blood pressure.

In some embodiments, the artery occlusion occurs at the brachial artery on the upper arm of the user and the method senses the pulsatile signal on the user's arm at a point below the pressure application site. For example, the method senses the pulsatile signal at the wrist or the finger of the user. The method determines the onset of the brachial diastolic blood pressure using the return to shape analysis.

In other embodiments, the artery occlusion occurs at the finger artery of the user and the method senses the pulsatile signal at the finger of the user. The method determines the onset of the finger diastolic blood pressure using the return to shape analysis. A transform function is applied to translate the finger diastolic blood pressure into diastolic blood pressure value for a target artery of the user, such as the brachial artery. For example, a transform function can be applied to translate the finger diastolic blood pressure measurement into a brachial diastolic blood pressure value.

In some embodiments, the method further determines the finger systolic blood pressure based on a return to flow analysis. In particular, the method detects the first beat after artery occlusion to indicate the onset of the systolic blood pressure. In the case where the artery occlusion occurs at the brachial artery, the method determines the onset of the brachial systolic blood pressure using the return to flow analysis. In the case where the artery occlusion occurs at the finger artery, the method determines the onset of the finger systolic blood pressure using the return to flow analysis. A transform function is applied to the finger systolic blood pressure to translate the finger systolic blood pressure into systolic blood pressure value for a target artery of the user, such as the brachial artery. For example, a transform function can be applied to translate the finger systolic blood pressure measurement into a brachial systolic blood pressure value.

In embodiments of the present disclosure, a blood pressure measuring device includes a pressure application element for applying controlled pressure to an application site on an arm of a user, a pulsatile signal sensor for sensing a pulsatile signal, and a controller/processor for controlling the pressure inflation and deflation and receiving and processing the sensed signal. The pressure application element applies controlled pressure to occlude blood flow to a target artery and releases the pressure at a certain rate under the control of the controller/processor. The pulsatile signal sensor detects a pulsatile signal as a result of the occlusion and subsequent pressure release. The processor implements a blood pressure measurement method in accordance with embodiments of the present disclosure to determine the systolic blood pressure, or the diastolic blood pressure, or both, from the detected beats in the sensed pulsatile signal. In some embodiments, the blood pressure measurement method determines the systolic blood pressure based on the return to flow analysis and determines the diastolic blood pressure based on the return to shape analysis.

In one embodiment, the blood pressure measuring device includes a brachial cuff as the pressure application element and the pulsatile signal sensor is configured to sense the pulsatile signal at the wrist or finger below the brachial cuff In another embodiment, the blood pressure measuring device includes a finger cuff. The pulsatile signal sensor and the controller/processor are integrated with the finger cuff.

The blood pressure measurement method and device of the present disclosure improves user experience by providing a more comfortable measurement scheme as compared to conventional blood pressure measurement methods. In some embodiments, the finger cuff can be integrated into a wearable device (for example attached to a wrist band or to a phone case, or other integration solutions), thus enabling users to frequently and more discreetly measure their blood pressure themselves. The blood pressure measurements can be electronically stored into the wearable device and may also be communicated to physicians (e.g. via a phone application), enabling users to better track their blood pressure and share their conditions with their health providers. Blood pressure is a key physiological parameter for people to understand their health state. By providing a wearable device with blood pressure measurement capability, frequent, easy blood pressure point estimation and tracking, and trending functions can be realized. This can provide the users with near-term, actionable information to adjust their behavior or treatment.

In some embodiments, the blood pressure measuring device of the present disclosure can be made in a compact device with the sensors integrated into the finger cuff. Measurements do not require multiple parts attached to the body. The blood pressure measuring device can be made as a portable standalone device or can be integrated with a wearable device. The blood pressure measuring device can be inexpensive and is easy to operate by a user. That is, the operation of the blood pressure measuring device does not require previous clinical knowledge. The blood pressure measuring device can be constructed to operate at low power consumption. Finally, the blood pressure measuring device can be configured to use a wide range of sensors that are sensitive to pulsation signals. The blood pressure measuring device of the present disclosure can encourage increased frequency of blood pressure monitoring, such as increased number of daily measurements or increased number of days for monitoring.

In particular, the blood pressure measurement method of the present disclosure implements a novel return to shape analysis to determine the diastolic blood pressure based on analysis of characteristics or features of the detected beats in comparison with baseline beat characteristics. The blood pressure measurement method of the present disclosure enables diastolic blood pressure to be accurately determined. In the case the blood pressure measurement method determines the finger diastolic blood pressure, the finger diastolic blood pressure thus determined can be correlated to the diastolic blood pressure of a target artery using a transform function to provide clinical relevant blood pressure values for the users.

FIG. 1, which includes FIGS. 1(a) to 1(c), illustrates blood pressure measuring devices which can be used to implement the blood pressure measurement method in embodiments of the present disclosure. In particular, FIGS. 1(a) to 1(c) illustrate different configurations of the blood pressure measuring device which can be used to implement the blood pressure measurement method in accordance with the present disclosure. The blood pressure measuring devices described herein enables noninvasive measurement and tracking of systolic and diastolic blood pressure. The embodiments shown in FIGS. 1(a) to 1(c) are illustrative only and not intended to be limiting. One of ordinary skill would appreciate that various modifications can be made to the blood pressure measuring devices described herein without departing from the scope of the present disclosure. In particular, FIGS. 1(a) to 1(c) illustrate blood pressure measuring devices for applying pressure to the finger artery. In other embodiments, the blood pressure measuring device may include a brachial cuff and a pulsatile signal sensor for measuring the pulsatile at the finger or wrist below the brachial cuff.

Referring first to FIG. 1(a), in a first embodiment, a blood pressure measuring device 10 includes a pressure application element 12, a pulsatile signal sensor 14 and a controller/processor 18. In some embodiments, the blood pressure measuring device 10 may further includes a pressure sensor 16 to measure the pressure being applied by the pressure application element 12. The pressure application element 12 is configured to accommodate a finger or a digit of a user.

In some embodiments, the blood pressure measuring device 10 is configured as a standalone device. That is, the blood pressure measuring device 10 can operate without being attached or linked to an external device. In a stand-alone configuration, the controller/processor 18 operates the blood pressure measuring device 10 on its own to inflate and deflate the pressure application element 12 and to control the pulsatile signal sensor 14 to collect and store sensed signals. The controller/processor 18 implements the blood pressure measurement method of the present disclosure to provide blood pressure measurement values based on the sensed signals. In some embodiments, the controller/processor 18 includes a wireless communication interface to enable the detected blood pressure values and/or the sensed signal data to be communicated wirelessly to another device.

In some embodiments, the blood pressure measuring device 10 can include user interface buttons, such as a button 20 for turning on or off the device 10 and a button 22 for initiating the blood pressure measurement method. The user interface buttons are optional and may be omitted in other configurations or may of the blood pressure measuring device.

In alternate embodiments, the blood pressure measuring device 10 is configured as an add-on device to an electronic device, such as a mobile device or a wearable device. In that case, the blood pressure measuring device 10 may further include a data bus 24 for connecting to an external electronic device, such as a user-wearable device, to communicate data and/or to receive control signals. In alternate embodiments, the blood pressure measuring device 10 may further include a tube 26 for providing air for pressure application. The data bus 24 and the tube 26 are optional and may be omitted in other embodiments of the present disclosure.

The pressure application element 12 operates to occlude blood flow in the arteries of the finger by applying direct pressure on the arteries and then slowly releasing the applied pressure. In one example, the pressure application element 12 may be a finger cuff disposed to be positioned onto a finger of the user, as shown in FIG. 1(c). The pulsatile signal sensor 14 is disposed inside the pressure application element 12 to detect pulsatile signals from the pressure application site, such as the finger. The processor 18 receives and processes the sensor signal from the pulsatile signal sensor 14 to generate the blood pressure measurement values.

In embodiments of the present disclosure, the controller/processor 18 can be part of the blood pressure measuring device or the processing function can be performed using the processor on the attached or linked electronic device. In some cases, the controller/processor 18 on the blood pressure measuring device 10 receives pulsatile signal from the subject and performs pre-processing of the pulsatile signal.

The pre-processed signal is then provided to an attached electronic device, such as by using the data bus 24, to be further processed by the processor on the electronic device to obtain the systolic and diastolic blood pressure values. In other cases, the controller/processor 18 receives and processes the pulsatile signal entirely to provide the systolic and diastolic blood pressure values.

In some embodiments, the pressure application element 12 may be configured with an automatic pressure release or the pressure release can be controlled by the user. In some embodiments, the pressure application element 12 is a finger cuff and the finger cuff can be an inflatable device. Furthermore, in some embodiments, the finger cuff can be in the form of a resizable ring, as shown in FIG. 1(a), or a semi-ring.

Furthermore, in alternate embodiments, as shown in FIG. 1(b), the finger cuff can be configured as a wrap around cuff. Referring to FIG. 1(b), a blood pressure measuring device 30 includes a pressure application element 32 formed as an open-ended cuff. The ends of the pressure application element 32 may be closed using any reattachable means, such as Velcro. The blood pressure measuring device 30 further includes a pulsatile signal sensor 34 and a controller/processor 38 formed on the finger cuff In some embodiments, the blood pressure measuring device 30 may further includes a pressure sensor 36. In some embodiments, the blood pressure measuring device 30 may include a data bus 44 for communication with an external device and a tube 46 for providing air for pressure application. The data bus 44 and the tube 46 are optional and may be omitted in other embodiments.

FIG. 1(c) illustrates a blood pressure measuring device 50 configured as a standalone unit. In that case, the blood pressure measuring device 50 can be accommodated onto a finger or digit of a subject without any wires or tubes. The standalone configuration of blood pressure measuring device 50 provides ease of use for the users and enable ready and frequent blood pressure monitoring by users.

In one example, the blood pressure measuring device of the present disclosure, shown in various embodiments in FIGS. 1(a) to 1(c), operates as follows. To perform a systolic/diastolic blood pressure measurement at the finger, the blood pressure measuring device 10 is attached to the finger of a user. The pressure application element 12/32 then applies pressure on the artery of the finger until a certain pressure level is reached such that the artery is totally occluded and no blood is flowing through the artery. Then, the pressure application element 12/32 decreases the applied pressure at a certain rate. In some embodiments, the pressure is released at a constant rate. The pulsatile signal sensor 14/34 senses the pulsatile signal during the deflation of the pressure application element 12. The processor 18/38, or a processor on an electronic device attached to the blood pressure measuring device, implements the blood pressure measurement method of the present disclosure to process the acquired pulsatile signal during the deflation phase and determine the finger systolic and diastolic blood pressure. The finger systolic and diastolic blood pressure values are translated into brachial pressure values using a transform function. In some cases, the measured values are presented to the user, or the values are stored, and or sent to a third party.

In particular, brachial blood pressure is the current gold standard for diagnosis/clinical management of blood pressure. The blood pressure measuring device of the present disclosure uses a transform function between the finger and the target artery (e.g. brachial, central, femoral, carotid) to estimate the pressure at the target artery. In this manner, the blood pressure measuring device of the present disclosure is capable of estimating the absolute blood pressure values of any artery in the body by measuring the finger blood pressure.

In one example, the transform function can be implemented using personal calibration. That is, the brachial and finger pressure of a user can be measured during several sessions and the measured values are fitted using a monotonic function. In another example, the transform function can be implemented using demographic studies. The transform function of different types of sub-populations (gender, age, height, weight, medical condition, etc.) can be collected. Data collection can be made on a relatively large population and the transform function is provided to the user and applied based on demographic factors. In this case, no calibration step will be required from the user.

In embodiments of the present disclosure, the pressure application element 12/32 can be implemented using an air inflation mechanism or a pneumatic system that inflates air into the pressure application element. In one example, the pressure application element is an inflatable finger cuff. The finger cuff may include an inflation mechanism or a pneumatic system that inflates air into the inflatable cuff.

In alternate embodiments, the pressure application element can be implemented using a compression mechanism to apply a direct force to the arteries to occlude the blood flow in the artery. In one example, the blood pressure measuring device is implemented as a mechanical spring. In other embodiments, other pressure application mechanisms that can occlude the blood flow in the finger arteries and can release a controllable amount of pressure can also be used.

In some embodiments, the pressure application element includes the internal pressure sensor 16/36 configured to measure the applied pressure. In one embodiment, the pressure application element 12/32 is able to apply a pressure of up to 300 mmHg. The pressure application element 12/32 is controlled, such as by the controller/processor 18/38 or by a processor of an attached electronic device, to apply pressure and to release the applied pressure at a pre-defined rate (such as 2 mmHg/sec) until reaching a nominal pressure value (e.g. 30 mmHg).

The blood pressure measuring device of the present embodiments includes the pulsatile signal sensor 14/34 configured to detect pulsatile information at the finger originating from the heart. The pulsatile signal sensor 14/34 can be implemented using any types of sensors that are able to measure blood pulsatile activity in the arteries. In some embodiments, the pulsatile signal sensor 14/34 is a photoplethysmogram (PPG) sensor. In other embodiments, the pulsatile signal sensor 14/34 can be a piezo electric/piezo resistive sensor or a ballistocardiogram (BCG) sensor. In yet other embodiments, the pulsatile signal sensor 14/34 is implemented as an electromagnetic radio-frequency (RF) based sensor, a laser based sensor, or an ultrasound sensor. In one example, the pulsatile signal sensor 14/34 is positioned on the bottom of the finger cuff to be in tactile contact with the finger surface opposite the finger nail.

FIG. 2, which includes FIGS. 2(a) to 2(c), illustrates another example of the blood pressure measuring device using a compression finger cuff. Referring to FIG. 2, a compression finger cuff 60 is constructed using a mechanical spring which occludes or compresses the finger arteries of a finger 63 positioned therein. FIG. 2(a) illustrates a front view of the compression finger cuff and FIG. 2(b) illustrates a side view of the compression finger cuff In some examples, the compression finger cuff can be incorporated into a mobile device 65 to enable portable measurement using the mobile device, as shown in FIG. 2(*c*).

In the embodiments described above, the blood pressure measuring device is configured to apply pressure to the finger artery and sense the pulsatile signal at the finger artery. In other embodiments, the blood pressure measuring device is configured using a brachial cuff or an arm cuff as the pressure application device. The brachial artery is occluded as a result of the application of pressure. Meanwhile, the pulsatile signal sensor is configured to measure the pulsatile signal from the wrist or the finger of the user. The controller/processor, which may be co-located with the pulsatile signal sensor or may be disposed on an attached electronic device, implements the blood pressure measurement method of the present disclosure to determine the diastolic blood pressure using the return to shape analysis. The resulting diastolic blood pressure measurement is the brachial blood pressure value and no transform function is needed.

In one example, the blood pressure measuring device using a brachial cuff operates as follows. To perform a systolic/diastolic blood pressure measurement, the blood pressure measuring device is attached to the upper arm of a user. The pressure application element then applies pressure on the brachial artery of the upper arm until a certain pressure level is reached such that the brachial artery is totally occluded and no blood is flowing through the brachial artery. Then, the pressure application element decreases the applied pressure at a certain rate. In some embodiments, the pressure is released at a constant rate. The pulsatile signal sensor senses the pulsatile signal at the wrist or finger below the brachial cuff during the deflation of the pressure application element. The processor, either co-located with the sensor or located on an electronic device attached to the blood pressure measuring device, implements the blood pressure measurement method of the present disclosure to process the acquired pulsatile signal during the deflation phase and determine the brachial systolic and diastolic blood pressure. In some cases, the measured values are presented to the user, or the values are stored, and or sent to a third party.

FIG. 3 illustrates a block diagram of a blood pressure measuring device in embodiments of the present disclosure. Referring to FIG. 3, a blood pressure measuring device 100 includes a pressure application element 128 to apply and release pressure to an application site of the user and a pulsatile signal sensor 136 to measure a pulsatile signal at a measurement site of the user. In one embodiment, the pulsatile signal sensor 136 is a PPG sensor. The blood pressure measuring device 100 may further include a pressure sensor 138 to measure the pressure being applied by the pressure application 128. The blood pressure measuring device 100 further includes a controller/processor 110 which operates as a controller to control the pressure application element 128 and the sensors 136, 138. The processor 110 receives and processes the signals sensed by the sensors 136, 138.

In the present embodiment, the processor 110 implements the blood pressure measurement method of the present disclosure to obtain blood pressure measurement values through pressure application and pulsatile signal detection. Accordingly, the processor 110 incorporates a detection module 120 to perform blood pressure measurement operations. In embodiments of the present disclosure, the detection module 120 includes a data processing module 122, a systolic blood pressure detection module 124, and a diastolic blood pressure detection module 126. The data processing module 122 is configured to perform signal preprocessing on the sensed pulsatile signal. For example, the data processing module 122 may perform baseline removal or DC signal level removal on the sensed pulsatile signals. In other embodiments, the data processing module 122 may perform beats detection and beats validation.

The systolic blood pressure detection module 124 implements analysis of the detected beats to determine the systolic blood pressure value. The diastolic blood pressure detection module 126 implements analysis of the detected beats to determine the diastolic blood pressure value. In the present embodiment, the detection module 120 includes detection modules for both the systolic blood pressure and the diastolic blood pressure. This configuration is illustrative only and not intended to be limiting. In some embodiments, the detection module 120 may include only the diastolic blood pressure detection module 126.

In alternate embodiments, the processor 110 may perform part of the signal processing, such as certain signal preprocessing, and provide the processed signal to an external device. The external device may implement the blood pressure measurement method of the present disclosure to obtain blood pressure measurement values. In embodiments of the present disclosure, the specific processor used to execute the blood pressure measurement method is not critical to the practice of the present disclosure.

In some embodiments, the controller/processor 110 is configured to control the pressure application operation, the sensing operation, the signal processing operation, and device communication events and other device-specific functions in the user-wearable device. In the present embodiment, the blood pressure measuring device 100 further includes a memory 130, a communication interface 132, and an input/output (I/O) interface 134. While the device 100 is described as comprising these various elements, other embodiments may use other architectures where the different functionalities are grouped differently. For example, the grouping may be in different integrated circuit chips. Or the grouping may be combining different elements such as the I/O interface 134 and the communication interface 132 together.

Figure 4:
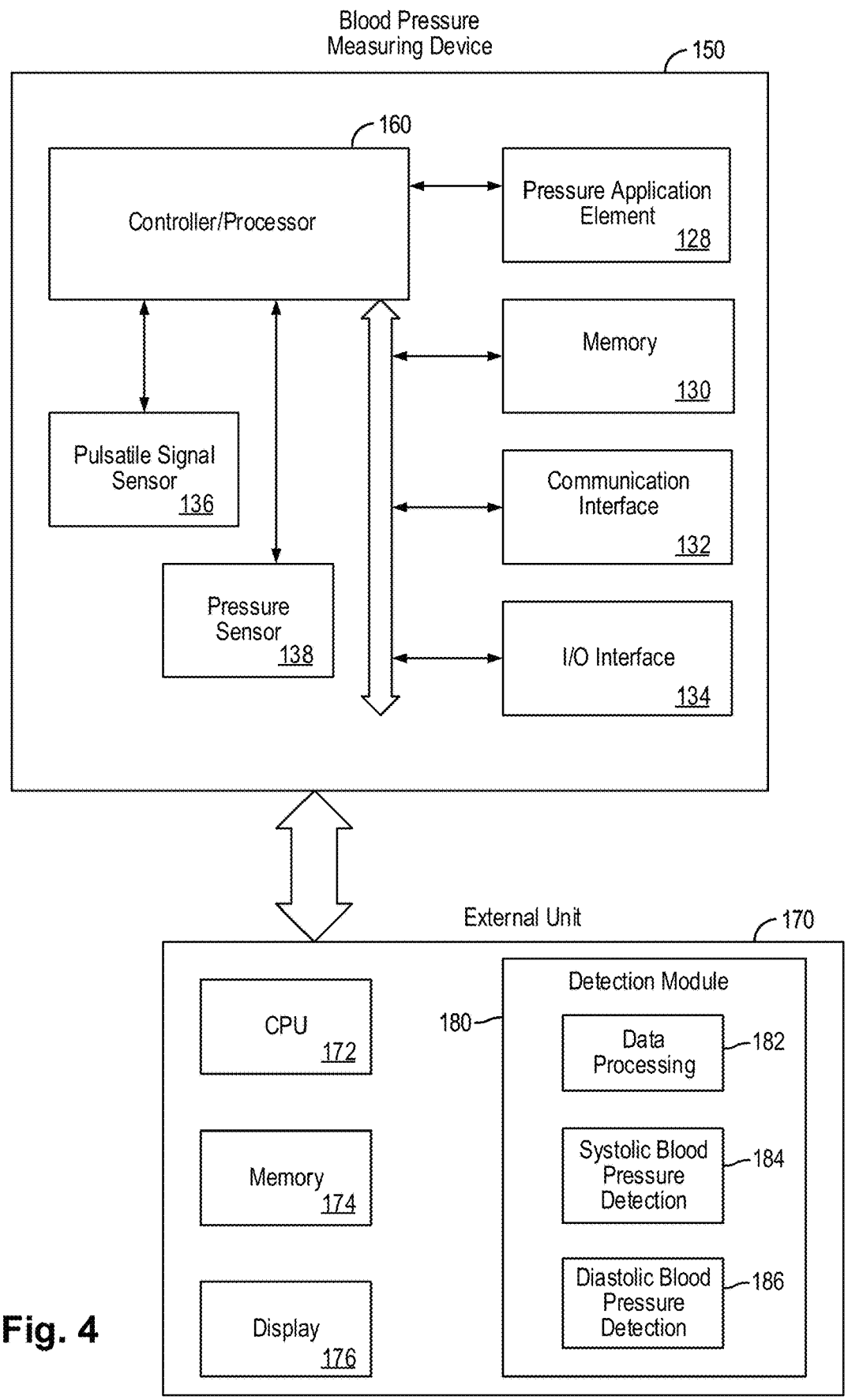
FIG. 4 illustrates a block diagram of a blood pressure measuring device in alternate embodiments of the present disclosure.

FIG. 4 illustrates a block diagram of a blood pressure measuring device in alternate embodiments of the present disclosure. Referring to FIG. 4, a blood pressure measuring device 150 is configured in a similar manner as the blood pressure measuring device 100 of FIG. 3 except that the detection module is provided in an external unit 170. The blood pressure measuring device 150 is in communication with the external unit 170, either through wired or wireless communication, and provides the sensed signals to the external unit 170 for processing to determine the blood pressure values. The external unit 170 includes a central processing unit (CPU) 172, a memory 174, and a display 176. The external unit 170 incorporates the detection module 180 for performing data processing and systolic and diastolic blood pressure detection in the manner described above. In one embodiment, the detection module 180 includes a data processing module 182, a systolic blood pressure detection module 184, and a diastolic blood pressure detection module 186.

Figure 5:
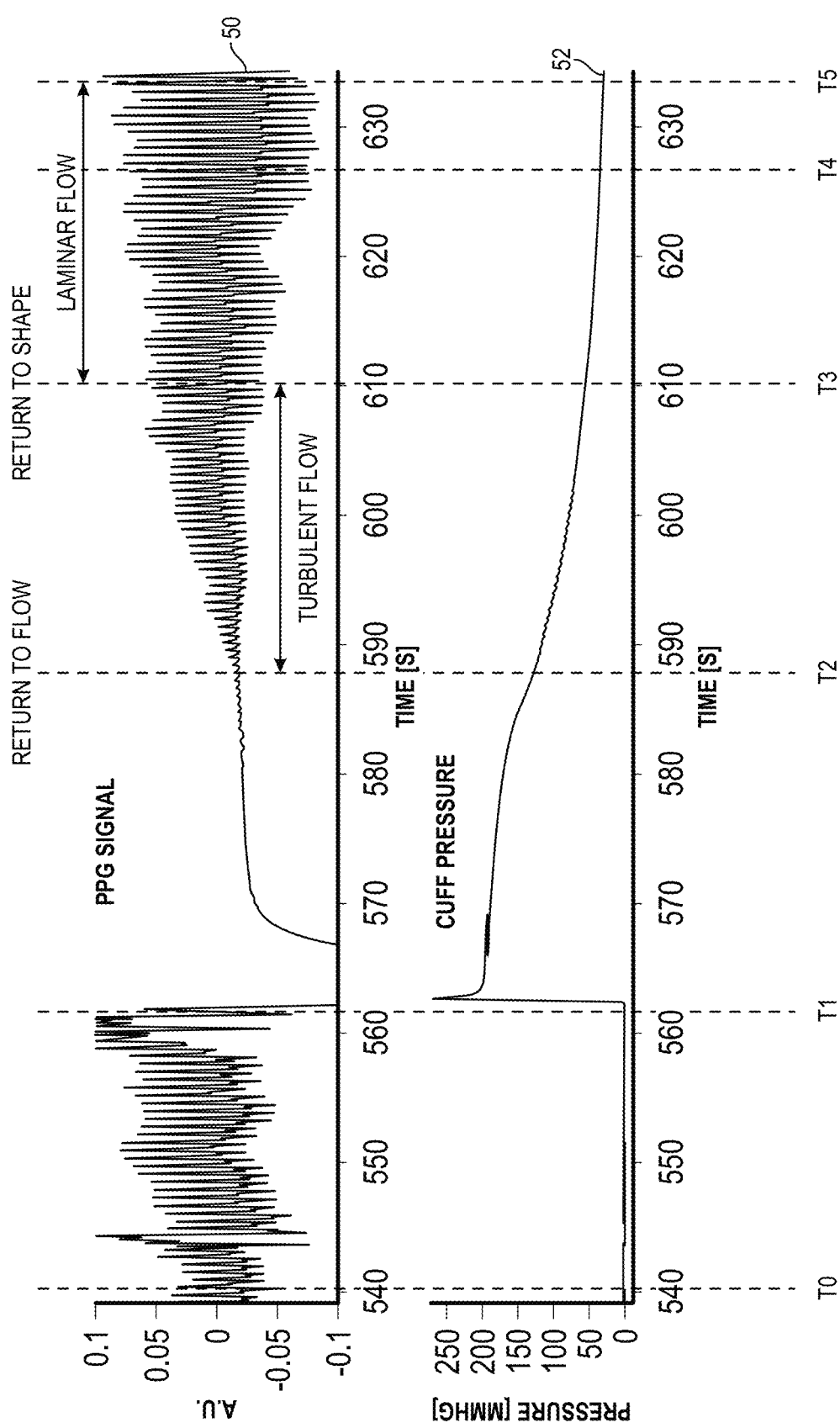
FIG. 5 illustrates a pulsatile signal waveform as a function of the pressure applied by the finger cuff illustrating the operation of the blood pressure measurement method of the present disclosure in some embodiments.

FIG. 5 illustrates a pulsatile signal waveform as a function of the pressure applied by the finger cuff illustrating the operation of the blood pressure measurement method of the present disclosure in some embodiments. Referring to FIG. 5, a curve 50 illustrates the pulsatile signal measured by the pulsatile signal sensor in response to the applied pressure to the artery where the applied pressure is illustrated by curve 52. In the present embodiment, the pulsatile signal waveform (curve 50) is obtained using a PPG sensor. In particular, FIG. 5 illustrates the "return to flow" phenomenon used to estimate the systolic pressure and the "return to shape" phenomenon used to estimate the diastolic blood pressure, as will be described in more detail below.

An example operation of the blood pressure measurement method is as follows. To perform a systolic/diastolic blood pressure measurement at the finger, the blood pressure measuring device is attached to the finger of the user, such as at the fingertip, the middle of the finger, or the upper part of the finger. The pulsatile signal sensor senses the pulsatile signal and the processor receives the sensed pulsatile signal and checks the validity or quality of the sensed signal. In the event the validity of the quality of the sensed signal is determined to be unacceptable, the blood pressure measuring device could alert the user that the blood pressure measuring device is not properly located or that the signal quality is not adequate to continue the measurement.

The measurement operation starts at time T0 with no pressure (0 mmHg) being applied and normal PPG signal is recorded, as shown by curve 50 between time T0 and T1. At time T1, the pressure application element or the finger cuff is operated to increase the applied pressure to a high pressure level sufficient to occlude the artery, that is, causing the blood to stop flowing in the artery. For example, the high pressure value can be in the range of 200-300 mmHg. In another example, the pressure application element or the finger cuff is operated to increase the applied pressure to a value 20-40 mmHg above the systolic pressure, for example 180 mmHg. The exact value of the high pressure level is not critical as long as the finger cuff fully occludes the artery in the finger. The occlusion by the finger cuff causes the pulsatile signal to disappear at time T1, as shown by the pulsatile signal waveform (curve 50) in FIG. 5.

After reaching the maximum applied pressure, the finger cuff pressure is released at a certain rate until reaching a minimum value or reaching the nominal pressure level (e.g. 30 mmHg) (curve 52). For example, the finger cuff pressure is released at a constant rate of 2 mmHg/sec. The pulsatile signal sensor detects for the pulsatile signal while the cuff pressure decreases. The processor processes the acquired pulsatile signal to determine the systolic and diastolic blood pressure values. The estimated systolic and diastolic blood pressure values can be stored on the blood pressure measuring device or provided to an attached electronic device or transmitted to an external device, a third party, or displayed to the user.

In embodiments of the present disclosure, the detection of the systolic blood pressure is based on the "return to flow" principle, meaning that the systolic pressure is defined as the onset of initial pulsatile activity in the acquired signal after total occlusion. For example, referring still to FIG. 5, at time T2, the first beat is detected after total occlusion of the artery. The applied cuff pressure at time T2 (e.g. 140 mmHg) is recorded as the finger systolic blood pressure. A transform function is applied to the finger systolic blood pressure measurement to convert the measurement to a brachial systolic blood pressure measurement.

In embodiments of the present disclosure, the detection of the diastolic blood pressure is based on the "return to shape" principle. The return to shape principle assumes that pulsatile signal waveforms that are created after the applied pressure on the artery is below the systolic pressure (after time T2), but above the diastolic pressure (before time T3), are distorted due to blood turbulences. That is, the artery experiences the turbulent flow property. However, the pulsatile signal waveforms obtained by the pulsatile signal sensor after the cuff pressure is below the diastolic blood pressure consist of predominantly the laminar flow property. Under the return to shape analysis, the diastolic blood pressure is determined by detecting significant enough changes between the acquired beat waveforms when a low or nominal pressure (e.g. below 30 mmHg) or no pressure is applied on the artery and acquired beat waveforms that are above 30 mmHg. The last beat that exhibits a significant change in beat characteristics from the baseline beat characteristics is defined as the onset of the diastolic blood pressure.

FIG. 6, which includes FIGS. 6(a) and 6(b), illustrates the turbulent and laminar blood flow characteristics in some examples. In embodiments of the present disclosure, the diastolic blood pressure is detected by determining a change in blood flow characteristic as the cuff pressure is being released. In particular, after total occlusion of the artery and no blood is flowing through the artery, the cuff pressure is gradually released, and blood flow returns to the artery. The blood pressure measurement method detects for the first beat after total occlusion as indicative of the return to flow which is indicative of the systolic blood pressure. During the period when the cuff pressure is below the systolic blood pressure but above the diastolic blood pressure, the artery experiences a turbulent blood flow, as shown in FIG. 6(a). When the cuff pressure release to below the diastolic blood pressure, the artery returns to a laminar blood flow, as shown in FIG. 6(b).

Turbulent blood flow affects various characteristics of the sensed pulse waveform. The blood pressure measurement method of the present disclosure detects the pulse waveform characteristics associated with laminar flow pulses to determine the diastolic blood pressure. That is, the method detects for a change in pulse waveform characteristics indicating a change from turbulent flow to laminar flow. The pulse waveform characteristics can include beat waveform shape, the DC level of the beat, the frequency content and other beat characteristics. The method associates the diastolic blood pressure with the cuff pressure at the onset of the detected change.

For example, returning to FIG. 5, after time T2, the artery experiences the turbulent blood flow. Eventually, when the applied pressure decreases to below the diastolic pressure, such as at time after T3, the artery experiences the laminar blood flow. The blood pressure measurement method of the present disclosure monitors and stores the sensed pulsatile signal from at least the onset of the systolic blood pressure until the end of measurement at time T5. In one example, after the applied pressure reaches the nominal pressure level (e.g. 30 mmHg or lower) at time T4, the blood pressure measurement method obtains the pulsatile signal after the pressure has dropped to the nominal pressure level (after time T4) to use to define the baseline beat characteristic. The baseline beat characteristic is described by a beat template which establishes the baseline values associated with the baseline beat characteristic. The beat template is then used to evaluate the pulsatile signal collected from time T1 to T4 to detect the onset of the beat that exhibits high similarity to the beat template. That is, the beats in the pulsatile signal are compared to the beat template to detect the beat with a beat property that is most similar to the beat template. The onset of the reached similarity point, T3, is defined as the onset of the finger diastolic pressure (e.g. 80 mmHg). In particular, the blood pressure measurement method senses the pulsatile signal during the turbulent blood flow period and during the laminar blood flow period during pressure deflation and the beat template is used to determine the transition from the turbulent flow period to the laminar flow period. The transition point (T3) is taken as the finger diastolic blood pressure. In some embodiments, the beats that are collected between time T0 and T1 are used the baseline beat waveforms to define the baseline beat characteristic or the beat template. That is, the beats before pressure application are used to form the beat template which enable real time determination of the finger diastolic blood pressure as the pressure is deflated during measurement.

In embodiments of the present disclosure, the blood pressure measurement method detects the finger diastolic blood pressure using the return to shape analysis. In some embodiments, the blood pressure measurement method may in additionally determine the finger systolic blood pressure using the return to flow analysis. In the following description, the blood pressure measurement method is described as performing both the systolic blood pressure measurement and the diastolic blood pressure. It is understood that the systolic blood pressure measurement is optional for the determination of the diastolic blood pressure and may be omitted in other embodiments of the present disclosure.

Figure 7:
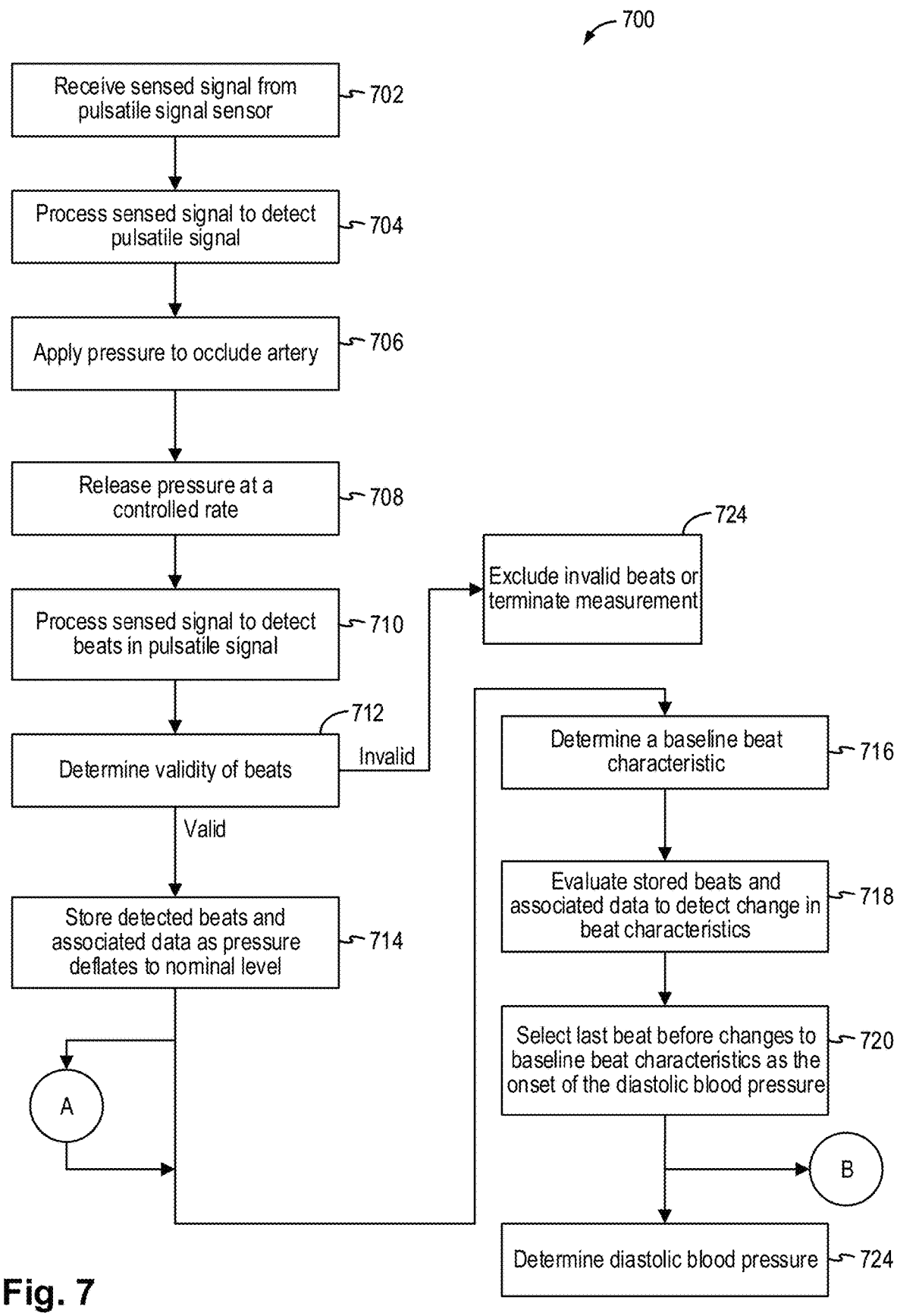
FIG. 7 is a flowchart illustrating a blood pressure measurement method in embodiments of the present disclosure.

FIG. 7 is a flowchart illustrating a blood pressure measurement method in embodiments of the present disclosure. In operation, the blood pressure measurement method is configured to monitor the pulsatile signal from the wrist or finger or digit of a user as pressure is being applied. For example, a finger cuff may be used to apply pressure to the user's finger and the pulsatile signal is collected from the user's finger. In another example, an arm cuff may be used to apply pressure the user's upper arm and the pulsatile signal is collected from the user's arm below the arm cuff, such as at the wrist or the finger. The cuff, whether finger cuff or arm cuff, may be inflated to a maximum pressure (e.g. 200 mmHg) and the cuff pressure may be deflated at a controlled rate until the pressure reaches the minimum pressure level or reaches below the nominal pressure level (e.g. 30 mmHg).

Referring to FIG. 7, a blood pressure measurement method 700 receives a sensed signal (702). The sensed signal can be obtained from a pulsatile signal sensor. For example, the pulsatile signal sensor is a PPG sensor and the sensed signal is a PPG signal. The method 700 processes the sensed signal to detect the pulsatile signal (704). The method 700 applies pressure to occlude an artery of the user (706). The artery can be a brachial artery or a finger artery. After reaching the maximum pressure (e.g. 200 mmHg), the method 700 the releases the pressure at a certain rate (708). Meanwhile, the method 700 receives sensed signal and detects beats in the sensed signal (710). In some embodiments, the method 700 applies a beat detector to determine the appearance of beats in the acquired signal segment. The method 700 then determines whether the detected beats are valid, according to their amplitude, morphology and the signal's noise level (712). When detected beats are deemed to be invalid, the method 700 may exclude the invalid beats or may terminate the measurement and notify the user (724).

As the pressure deflates at a certain rate, the method 700 receives the sensed signal and detects for beats in the pulsatile signal. The method 700 stores the valid detected beats and data associated with the valid detected beats in the sensed pulsatile signal as the pressure deflates towards the nominal pressure level (e.g. 30 mmHg) or below (714).

Detecting Finger Systolic Blood Pressure (Return to Flow)

Figure 8:
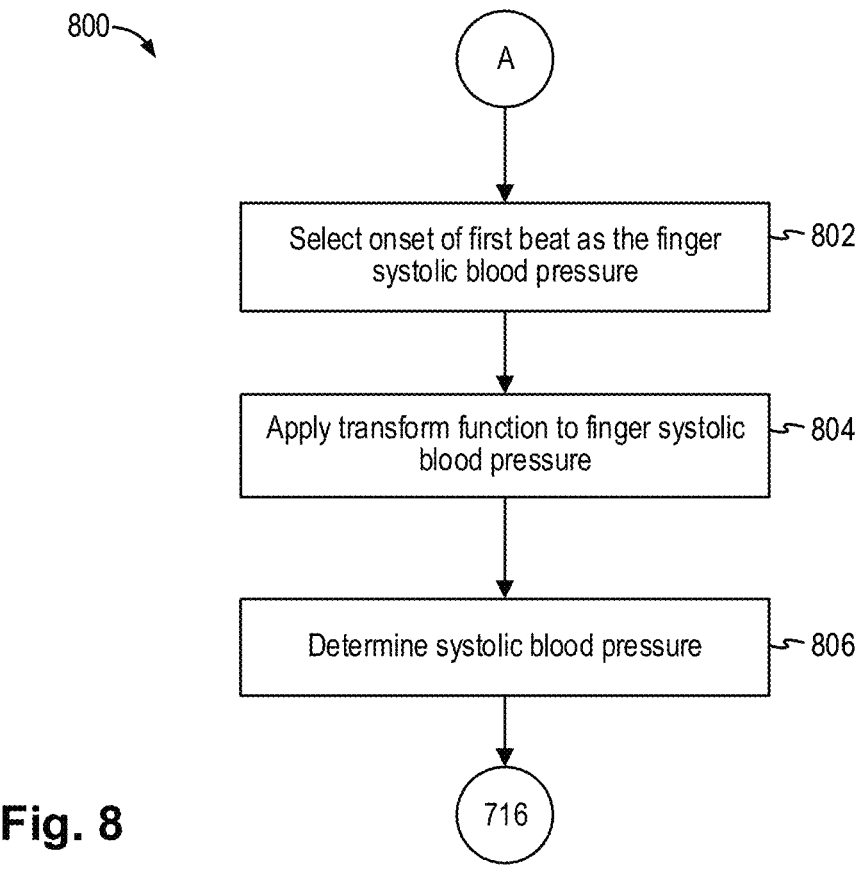
FIG. 8 is a flowchart illustrating the return to flow detection method in some embodiments.

In embodiments of the present disclosure, the onset of the systolic blood pressure is defined as the onset of the "return to flow" of the pulsatile signal. In embodiments when method 700 is configured to detect the systolic blood pressure in addition to the diastolic blood pressure, the method 700 continues to the process at "A". FIG. 8 is a flowchart illustrating the return to flow detection method in some embodiments. In the present embodiment, it is assumed the method is configured to apply pressure to the finger of the user. Referring to FIG. 8, the method 800 determines the onset of the finger systolic blood pressure as the first valid detected beat after total occlusion (802). This beat indicates the return to flow of the blood in the artery. For example, the onset time location of the first valid detected beat is used to derive the applied pressure value using the rate of pressure decrease. Alternately, readings from the pressure sensor can be used to determine the pressure value at the first valid detected beat. In some embodiments, the onset of the first valid detected beat is detected on-the-fly, that is, the first valid beat is detected as the pulsatile signal is being received and processed while the cuff pressure is being deflated. In other embodiments, the onset of the first valid detected beat is detected after the method 700 (FIG. 7) collects and stores all of the detected beats and the associated data, that is after end of measurement. The method 800 then search for the first valid beat from the stored beats.

After detecting the onset of the first beat and associating the pressure as the finger systolic blood pressure, the method 800 applies a transform function to translate the finger systolic pressure to a brachial systolic pressure value (804). For example, the transform function can be a finger to brachial transform function. The method 800 then determines the systolic blood pressure for the subject under test (806). After detection of the systolic blood pressure, the method 800 returns to method 700.

In summary, the systolic blood pressure is detected by determining the return of blood flow after total occlusion. After total occlusion of the artery and no blood is flowing through the artery, the cuff pressure is gradually released, and the method detects for the return to flow of the blood by detecting the first beat in the sensed signal. In one example, the return to flow method measures the signal-to-noise level during full occlusion. Then, the return to flow method detects for beats after cuff pressure release. The return to flow method may normalize the detected beats amplitude using the signal-to-noise level detected during full occlusion. The return to flow method detects the first beat as the beat with an amplitude that is greater than the noise level by a given factor, for example, greater than x times the noise level. In the case the occlusion is applied to the finger of the user, the return to flow method associates the finger systolic blood pressure with the cuff pressure at the onset of the first detected beat. The finger systolic blood pressure is converted to a brachial systolic blood pressure value using a transform function.

Detecting the Finger Diastolic Blood Pressure (Return to Shape)

Returning to FIG. 7, the method 700 stores valid detected beats and data associated with the detected beats from the sensed pulsatile signal as the pressure deflates towards the nominal pressure level (714). After all of the beats have been detected, the method 700 can then determine the diastolic blood pressure. The onset of the diastolic blood pressure is defined as the onset of the "return to shape" of the pulsatile signal.

In operation, the blood pressure measurement method 700 assumes that pulsatile waveforms and beat properties are distorted or altered when the cuff pressure is higher than the diastolic pressure, in comparison to the beats properties when the cuff pressure is lower than the diastolic pressure.

After the applied pressure drops below the diastolic pressure, the pulsatile signal waveforms and beat properties fully return to their baseline shape/value and remain similar afterwards. The "return to shape" method makes use of the full/partial beat's information, such as beat waveform shape, the DC level, the frequency content, and other beat properties, and uses various distance metrics to determine when the detected beats exhibit a significant change in waveform properties. The beat prior to the beat at which one or more beat properties exhibit significant similarity to the baseline beat properties is taken as the onset of the diastolic blood pressure. In the present description, a beat property is significantly similar to the baseline beat property where the beat property is nearly the same as or very close to the baseline beat property.

Referring to FIG. 7, the blood pressure measurement method 700 determines one or more baseline beat characteristics (716). In one embodiment, the blood pressure measurement method 700 determines a beat template indicating beat characteristics with no applied pressure or nominal applied pressure. In one example, the beat template can be derived from the beats detected after the cuff pressure has decreased to the nominal pressure level (e.g. 30 mmHg) or below. In another example, the beat template can be derived from the beats detected before any pressure is applied, such as during the initial measurement phase. For example, referring to FIG. 5, the beat template can be derived from the beats detected after time T4 or before time T1.

Figure 10:
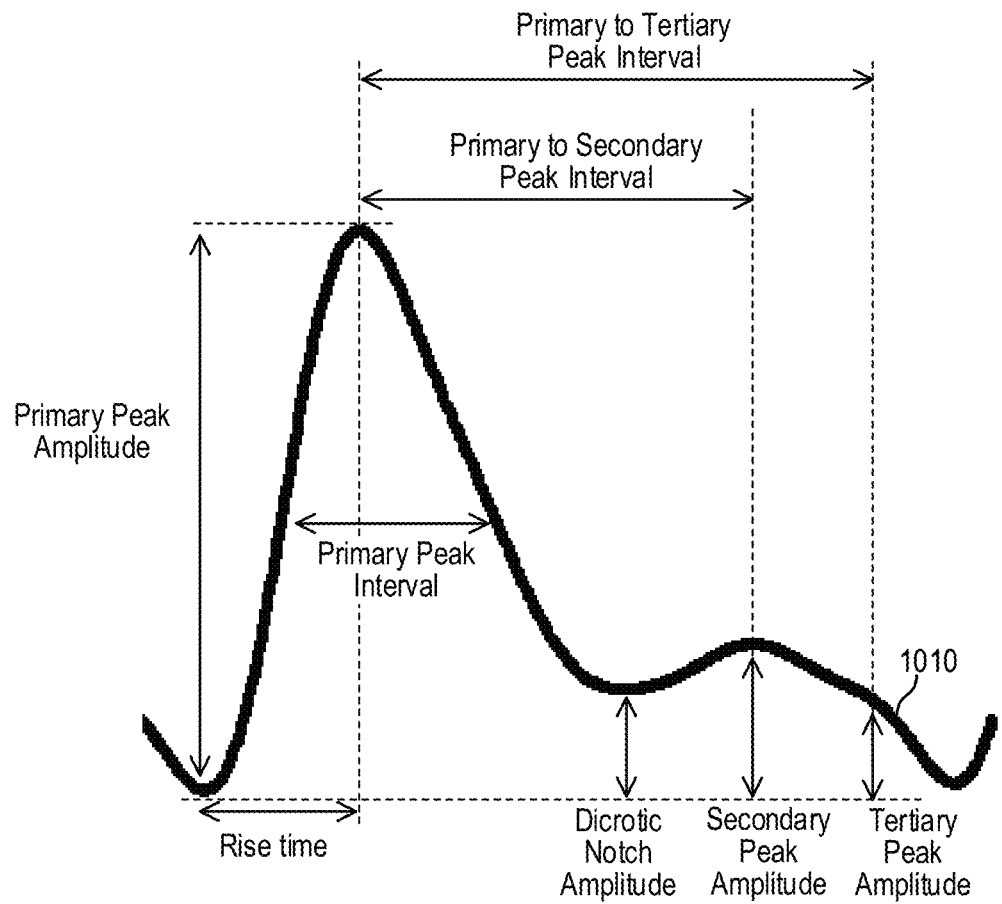
FIG. 10 illustrates an exemplary pulse waveform in some examples.

In particular, the beat template can be derived based on the entire or partial characteristics of the beat and can use various features of the beat waveform, such as the time domain characteristics or the frequency domain characteristics. FIG. 10 illustrates an exemplary pulse waveform in some examples. Referring to FIG. 10, a pulse or a detected beat 1010 exhibits various waveform characteristics which can be used to characterize the baseline waveform properties. In some embodiments, the pulse 1010 can be characterized by one of more of the following beat characteristics or features: the primary peak amplitude, the secondary peak amplitude, the tertiary peak amplitude, the rise time of the beat, the primary peak interval, the secondary peak interval, the tertiary peak interval, the primary to secondary peak interval, the primary to tertiary peak interval, the secondary to tertiary peak interval, the amplitude of the dicrotic notch, the amplitude of the tertiary notch, the interval from the first or second or third peak to the dicrotic or tertiary notch, the area under the curve defined by the pulse waveform, the area under the first or second or tertiary beat waveform peak, the acceleration time of the first or second or tertiary peak, and other parameters. In yet other embodiments, the pulse 1010 can be characterized by one of more frequency domain characteristics as the beat features. That is, the pulse 1010 can be analyzed in the frequency domain to determine the frequency content to use as the baseline waveform properties. In one embodiment, for each parameter or feature selected to characterize the pulse waveform, an associated beat template is defined.

In some embodiments, the method uses one or more of the following primary beat features for the return to shape analysis: (1) an area under the beat waveform of a beat; (2) an area under a second peak of the beat waveform; (3) an amplitude of a dicrotic notch of the beat waveform; and (4) a time interval between first and second peaks of the beat waveform.

Returning to FIG. 7, using the baseline beat characteristic, the method 700 evaluates the stored beats and associated data to detect for change in beat characteristics (718). In some embodiments, the method 700 segments the beats from the beginning of the cuff pressure release to the end of the measurement and the beats are evaluated segment by segment.

Furthermore, in some embodiments, the method 700 evaluates the stored beats by going backward in time from the last measured beat to earlier measured beats. The method 700 evaluates the beats to determine the beat with a feature change from the beat template. The last beat with characteristics different from the beat template defines the onset of the diastolic pressure. In another embodiment, the method 700 evaluates the stored beats by going forward in time from an earlier measured beat to the last measured beat. The method 700 evaluates the beats and the associated data to determine the last beat with characteristics different from the beat template. The last beat with characteristics different from the beat template defines the onset of the diastolic pressure.

As described above, the method 700 selects the last beat before change to the beat template is detected as the onset of the diastolic blood pressure (720). In one embodiment, the method 700 selects the last beat that is different from the beat template as the onset of the diastolic blood pressure. In this manner, the method 700 detects the last beat that is in the turbulent phase before the blood flow changes to laminar flow, from which the beat template is created. The method 700 determines the diastolic blood pressure value using the blood pressure value associated with the onset of the last beat before waveform change to the beat template (724).

Figure 12:
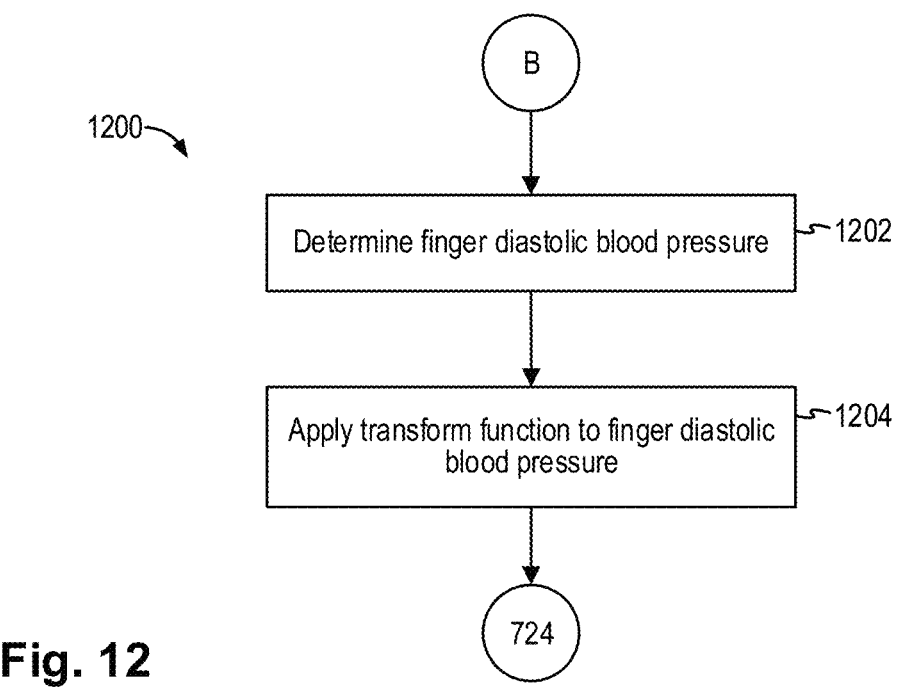
FIG. 12 is a flowchart illustrating a method for converting finger diastolic blood pressure in some embodiments.

In some embodiments, the method 700 is configured to apply pressure to an artery in the finger. In that case, the onset of the last beat before waveform change to the beat template is an indication of the finger diastolic blood pressure. In that case, the method 700 may continue to the process at "B". FIG. 12 is a flowchart illustrating a method for converting finger diastolic blood pressure in some embodiments. Referring to FIG. 12, the method 1200 determines the finger diastolic blood pressure from the return to shape analysis (1202). The method 1200 applies a finger to brachial transform function to translate the finger diastolic blood pressure to a brachial diastolic blood pressure (1204). As a result, the method 1200 determines the diastolic blood pressure for the brachial artery (724).

In embodiments of the present invention, the conversion using the transform function is not required when the pressure is applied to the brachial artery. The method 1200 in FIG. 12 is omitted in the case the pressure is applied to the brachial artery.

Figure 9:
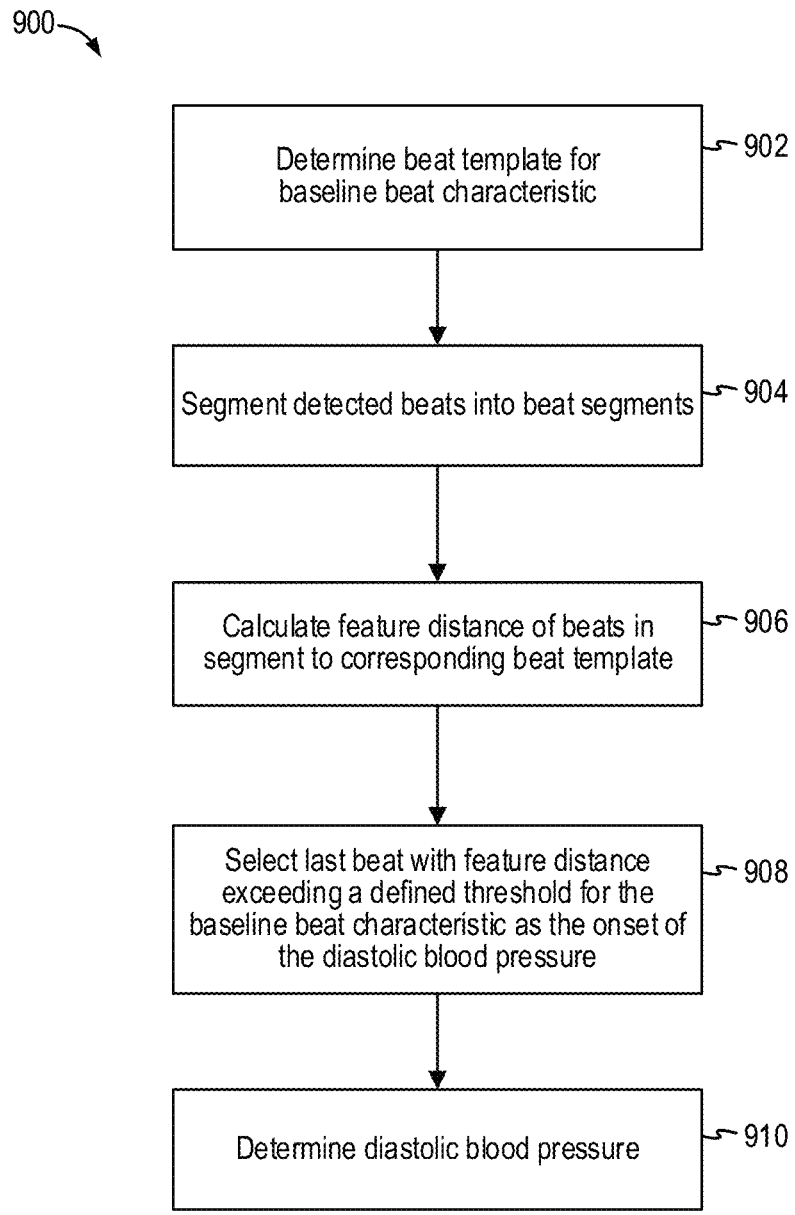
FIG. 9 is a flowchart illustrating the method for determining return to shape in some embodiments.

FIG. 9 is a flowchart illustrating the method for determining return to shape in some embodiments. Referring to FIG. 9, method 900 determines a beat template for each of one or more baseline beat characteristic (902). The beat template describes the baseline beat characteristic for the associated beat feature. The baseline beat characteristic refer to the beat characteristic with no pressure or nominal pressure (e.g. 30 mmHg) applied to the artery. The method 900 then segments the detected beats into beat segments (904). In some embodiments, the segmentation can be omitted.

The method 900 then compares the beats in each beat segment to the beat template. The method 900 calculates feature distances of the beats in the segment to the corresponding beat template (906). The method 900 selects the last beat with feature distance exceeding a defined threshold for the beat feature as the onset of the diastolic blood pressure (908). In some embodiments, the method 900 may use a lower limit and the last beat with feature distance greater than the lower threshold is selected as the onset of the diastolic blood pressure. In other embodiments, the method 900 may use an upper threshold and the last beat with feature distance less than the upper threshold is selected as the onset of the diastolic blood pressure. The method 900 determines the diastolic blood pressure value using the blood pressure value associated with the onset of the last beat as determined previously (910). In some embodiment, the pressure is applied to a finger artery and the method 900 may transform the finger diastolic blood pressure to brachial diastolic blood pressure using a finger to brachial transform function.

FIG. 11, which includes FIGS. 11(a) to 11(c), illustrates the return to shape operation in some examples. In the present embodiment, the blood pressure measurement method removes low frequency component in the measured signal, which is influenced by respiration. The method then segments the beats after cuff pressure decreases. The method normalizes the amplitude of the beats, as shown in FIG. 11(a). In FIG. 11(a), the beat template is illustrated by the thick dotted line and the non-template beats are shown as thin solid lines. The method defines template beats as beats associated with cuff blood pressure below the nominal pressure level (such as <30 mmHg). In FIGS. 11(b) and 11(c), the template beats are shown as solid black dots and the non-template beats are shown as outlined dots. In the present example, the method calculates the normalized area under the normalized beat waveform, as shown in FIG. 11(b). In other examples, other PPG features can also be used. The method calculates the distance of non-template beats from the template beats (in feature domain using a distance matrix), as shown in FIG. 11(c). The method detects abrupt changes in distance, such as more than between the template beats, as the indication of the diastolic blood pressure, as shown in FIG. 11(c).

Alternate Embodiments

In other embodiments, the onset of the "return to flow" and "return to shape" phenomena could be determined by the methods described above or other methods, presently known or to be developed. Other signal processing methods, including other algorithm heuristics or machine learning/deep learning implementations can also be used.

In embodiments of the present invention, a method for estimating blood pressure of a user by using a blood flow occlusion system applied to an artery in the body of the user implements the return to shape analysis to determine the diastolic blood pressure of the artery.

In some embodiments, the method further includes evaluating the detected beats to select a first beat after occlusion of the blood flow in the finger as the onset of the finger systolic blood pressure; determining a value of the applied pressure at the first beat as the finger systolic blood pressure; applying the transform function to translate the finger systolic blood pressure to a systolic blood pressure of a target artery; and providing the systolic blood pressure for the target artery as an output.

In other embodiments, the method applies a transform function that is personalized for a user or generalized across population or based on demographic studies.

In other embodiments, the applied pressure at the nominal level includes an applied pressure of 30 mmHg.

In other embodiments, the method evaluates detected beats and associated data to detect change in beat characteristics as compared to the baseline beat characteristics by segmenting the detected beats into beat segments; comparing beats in each segment to the beat template; determining feature distances of beats in a segment to the beat template; and selecting the beat with feature distance exceeding a first threshold for the feature as the last beat indicating the onset of the diastolic blood pressure for the artery.

Aspects of this disclosure are described herein with reference to flowchart illustrations or block diagrams, in which each block or any combination of blocks may be implemented by computer program instructions. The instructions may be provided to a processor of a general purpose computer, special purpose computer, or other programmable data processing apparatus to effectuate a machine or article of manufacture, and when executed by the processor the instructions create means for implementing the functions, acts or events specified in each block or combination of blocks in the diagrams.

In this regard, each block in the flowchart or block diagrams may correspond to a module, segment, or portion of code that includes one or more executable instructions for implementing the specified logical function(s). It should also be noted that, in some alternative implementations, the functionality associated with any block may occur out of the order noted in the figures. For example, two blocks shown in succession may, in fact, be executed substantially concurrently, or blocks may sometimes be executed in reverse order.

A person of ordinary skill in the art will appreciate that aspects of this disclosure may be embodied as a device, system, method or computer program product. Accordingly, aspects of this disclosure, generally referred to herein as circuits, modules, components or systems, may be embodied in hardware, in software (including firmware, resident software, micro-code, etc.), or in any combination of software and hardware, including computer program products embodied in a computer-readable medium having computer-readable program code embodied thereon.

The above detailed descriptions are provided to illustrate specific embodiments of the present disclosure and are not intended to be limiting. Numerous modifications and variations within the scope of the present disclosure are possible. The present disclosure is defined by the appended claims.

What is claimed is:

1. A method for estimating blood pressure of a user, the method comprising:
providing a cuff that is shaped to stay wrapped around a body part of the user that contains an artery, the artery being one of a finger artery, a radial artery, and a brachial artery, wherein the cuff includes a pressure application element configured to inflate and deflate to increase and decrease pressure on the artery, respectively;
attaching a pulsatile signal sensor to the cuff;
attaching a processor to the cuff, the processor activating the pulsatile signal sensor during the time the pressure application element is decreasing the pressure on the artery after occlusion;
receiving, from the pulsatile signal sensor, the pulsatile signal from the artery in response to releasing the pressure;
processing, via the processor, the pulsatile signal to detect beats;
determining, via the processor, validity of the detected beats;
storing, via the processor, the detected beats and data associated with the detected beats in the pulsatile signal;

obtaining, via the processor, baseline beats indicative of a baseline beat characteristic of the user;

normalizing, via the processor, the baseline beats to obtain template beats in a normalized domain;

normalizing, via the processor, the stored detected beats to obtain normalized beats in the normalized domain;

comparing, via the processor, the normalized beats and the template beats to detect a change in beat characteristics in the normalized domain with respect to an area or a distance from the template beats;

selecting, via the processor, a beat before the detected change in the beat characteristic as a last beat indicating an onset of a diastolic blood pressure for the artery;

determining, via the processor, a value of the applied pressure at the last beat as the diastolic blood pressure for the artery; and providing, in real time as the pressure is being released, the diastolic blood pressure as an output.

2. The method of claim 1, wherein selecting the beat before the detected change in the beat characteristic as the last beat indicating the onset of the diastolic blood pressure comprises:

selecting a beat before the beat at which an associated beat property exhibits similarity to the baseline beat characteristic as the last beat indicating the onset of the diastolic blood pressure for the artery.

3. The method of claim 1, wherein determining the value of the applied pressure at the last beat as the diastolic blood pressure comprises determining the value of the applied pressure at the last beat as a finger diastolic blood pressure, the method further comprising:

applying a transform function to translate the finger diastolic blood pressure to a diastolic blood pressure of a target artery; and providing the diastolic blood pressure value for the target artery as an output.

4. The method of claim 1, wherein determining the value of the applied pressure at the last beat as a finger diastolic blood pressure comprises:

determining a time location associated with the onset of the last beat; and determining the value of the applied pressure using the time location and the rate of pressure release.

5. The method of claim 1, wherein the baseline beats are obtained using the stored beats after the applied pressure has decreased to below a nominal level.

6. The method of claim 1, wherein the baseline beats are obtained before the pressure is applied to the artery.

7. The method of claim 1, wherein the template beats in the normalized domain are selected based on one of an area under a beat waveform of a beat, an area under a second peak of the beat waveform, an amplitude of a dicrotic notch of the beat waveform, and a time interval between first and second peak of the beat waveform.

8. The method of claim 1, wherein comparing the normalized beats and the template beats comprises:

evaluating the detected beats and the associated data in a backward time fashion from a beat before the last detected beat to earlier detected beats.

9. The method of claim 1, wherein comparing the normalized beats and the template beats comprises:

evaluating the detected beats and the associated data in a forward time fashion from earlier detected beats to the last detected beat.

10. The method of claim 1, wherein the pulsatile signal sensor is one of a photoplethysmogram (PPG) sensor, a piezo electric sensor or a piezo resistive sensor, or a ballistocardiogram (BCG) sensor, or an electromagnetic radio-frequency (RF) based sensor, a laser based sensor, and an ultrasound sensor.

11. The method of claim 1, wherein the pressure is applied to the brachial artery and the pulsatile signal is received from the finger or a wrist of the user, and wherein determining the value of the applied pressure at the last beat as the diastolic blood pressure comprises determining the value of the applied pressure at the last beat as the brachial diastolic blood pressure.

12. The method of claim 1, wherein selecting the beat before the detected change in the beat characteristic as the last beat indicating the onset of the diastolic blood pressure for the artery comprises selecting a beat immediately before the detected change in the beat characteristic as the last beat indicating the onset of the diastolic blood pressure for the artery.

13. A blood pressure measuring device comprising:

a cuff or ring shaped to stay wrapped around a user's bodypart containing an artery, the artery being one of a finger artery, a radial artery, and a brachial artery, wherein the cuff includes a pressure application element configured to apply pressure to the artery and to release the pressure;

a pulsatile signal sensor attached to the cuff or the ring and configured to sense a pulsatile signal from the artery during release of the pressure; and a processor configured to:

receive from the pulsatile signal sensor a pulsatile signal;

process the pulsatile signal to detect beats;

determine validity of the detected beats;

store the detected beats and data associated with the detected beats in the pulsatile signal as the pressure applied to the artery is reduced;

obtain baseline beats indicative of a baseline beat characteristic of the user;

normalize the baseline beats to obtain template beats in a normalized domain;

normalize the stored detected beats to obtain normalized beats in the normalized domain;

compare the normalized beats and the template beats to detect a change in beat characteristics in the normalized domain with respect to an area or a distance from the template beats;

select a beat before the detected change in the beat characteristic as a last beat indicating an onset of a diastolic blood pressure for the artery;

determine a value of the applied pressure at the last beat as the diastolic blood pressure for the artery; and provide, in real time as the pressure is being released, the diastolic blood pressure as an output.

14. The blood pressure measuring device of claim 13, wherein the processor is further configured to:

select a beat before the beat at which an associated beat property exhibits similarity to the baseline beat characteristic as the last beat indicating the onset of the diastolic blood pressure for the artery.

15. The blood pressure measuring device of claim 13, wherein the pressure application element is configured to apply pressure to the artery and the pulsatile sensor is configured to receive the pulsatile signal from the finger of the user, and determining the value of the applied pressure at the last beat as the diastolic blood pressure comprises determining the value of the applied pressure at the last beat as a finger diastolic blood pressure, the processor being further configured to:

apply a transform function to translate the finger diastolic blood pressure to a diastolic blood pressure of a target artery; and provide the diastolic blood pressure value for the target artery as an output.

16. The blood pressure measuring device of claim 13, wherein the processor is further configured to:

obtain the baseline beats using the stored beats after the applied pressure has decreased to below the nominal level.

17. The blood pressure measuring device of claim 13, wherein the processor is further configured to:

obtain the baseline beats before the pressure is applied to the artery of the user.

18. The blood pressure measuring device of claim 13, wherein the processor is further configured to:

select the template beats in the normalized domain based on one of an area under a beat waveform of a beat, an area under a second peak of the beat waveform, an amplitude of a dicrotic notch of the beat waveform, and a time interval between first and second peak of the beat waveform.

19. The blood pressure measuring device of claim 13, wherein the blood pressure measuring device is a standalone device.

20. The blood pressure measuring device of claim 13, wherein the pulsatile signal sensor comprises one of a photoplethysmogram (PPG) sensor, a piezo electric sensor or a piezo resistive sensor, or a ballistocardiogram (BCG) sensor, or an electromagnetic radio-frequency (RF) based sensor, a laser based sensor, and an ultrasound sensor.

21. The blood pressure measuring device of claim 13, further comprising a pressure sensor configure to sense the applied pressure.

22. A method for estimating blood pressure of a user, the method comprising:

applying, via a pressure application element, a pressure to an artery of a finger of the user and releasing the pressure;

receiving, via a photoplethysmogram (PPG) sensor, a PPG signal from the artery during the releasing of the pressure;

processing, at a processor, the PPG signal to detect beats;

determining, via the processor, validity of the detected beats;

storing the detected beats and data associated with the detected beats in the PPG signal as the pressure applied to the artery is reduced towards a level below a nominal level;

obtaining, via the processor, baseline beats indicative of a baseline beat characteristic of the user;

normalizing, via the processor, the baseline beats to obtain template beats in a normalized domain;

normalizing, via the processor, the stored detected beats to obtain normalized beats in the normalized domain;

comparing, via the processor, the normalized beats and the template beats to detect a change in beat characteristics in the normalized domain with respect to an area or a distance from the template beats;

selecting, via the processor, a beat before the detected change in the beat characteristic as a last beat indicating an onset of a finger diastolic blood pressure for the artery;

determining, via the processor, a value of the applied pressure at the last beat as the finger diastolic blood pressure; and providing, in real time as the pressure is being released, the finger diastolic blood pressure as an output.

23. The method of claim 22, further comprising:

applying a transform function to translate the finger diastolic blood pressure to a diastolic blood pressure of a target artery; and providing a value of the diastolic blood pressure for the target artery as an output.

24. The method of claim 23, further comprising:

evaluating the stored beats and the associated data to select a first beat after occlusion of the blood flow in the finger as the onset of a finger systolic blood pressure;

determining the value of the applied pressure at the first beat as the finger systolic blood pressure;

applying the transform function to translate the finger systolic blood pressure to a systolic blood pressure of the target artery; and providing the systolic blood pressure for the target artery as an output.

* * * * *